US00PP23938P2

(12) United States Plant Patent
Verschoor

(10) Patent No.: US PP23,938 P2
(45) Date of Patent: Oct. 1, 2013

(54) ***VERONICA* PLANT NAMED 'ATOMIC SILVERY PINK RAY'**

(50) Latin Name: *Veronica hybrida*
Varietal Denomination: Atomic Silvery Pink Ray

(76) Inventor: Jan Verschoor, Haarlem (NL)

( * ) Notice: Subject to any disclaimer, the term of this patent is extended or adjusted under 35 U.S.C. 154(b) by 0 days.

(21) Appl. No.: 13/506,896

(22) Filed: May 23, 2012

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Kent L Bell
(74) *Attorney, Agent, or Firm* — Audrey Charles

(57) ABSTRACT

A new and distinct cultivar of *Veronica* plant named 'Atomic Silvery Pink Ray', particularly distinguished by pink colored flowers, floriferous with healthy foliage, good mildew resistance, and well-branched, compact growth habit, is disclosed.

1 Drawing Sheet

Latin name of genus and species of plant claimed: *Veronica hybrida.*

Variety denomination: 'Atomic Silvery Pink Ray'.

BACKGROUND OF THE INVENTION

The present invention relates to a new and distinct cultivar of *Veronica* plant botanically known as *Veronica hybrida* and hereinafter referred to by the cultivar name 'Atomic Silvery Pink Ray'. The new cultivar originated from an open pollination in 2005 in a nursery location in Haarlem, The Netherlands between unknown male and female *Veronica hybrida* plants. The objective of the breeding program was the development of *Veronica* cultivars with improved branching, unique flower coloration, and compact habits.

The new cultivar was selected from the results of the open pollination in 2007 in Haarlem, The Netherlands. Asexual reproduction of the new *Veronica* by vegetative cuttings in a controlled environment in Haarlem, The Netherlands since the summer of 2007, has shown that the unique features of the *Veronica* are stable and reproduced true to type in successive generations.

SUMMARY OF THE INVENTION

The following are the most outstanding and distinguishing characteristics of this new cultivar when grown under normal horticultural practices in Haarlem, The Netherlands:

1. Pink-colored flowers;
2. Floriferous with healthy foliage;
3. Good mildew resistance; and
4. Well-branched, compact growth habit.

Of the many commercially available *Veronica* cultivars, the most similar in comparison to the new cultivar is 'Atomic Pink', U.S. Plant Pat. No. 21,797. However, in side by side comparisons in Haarlem, The Netherlands, plants of the new cultivar 'Atomic Silvery Pink Ray' differ from plants of 'Atomic Pink' in at least flower color. Plants of 'Atomic Silvery Pink Ray' have a flower color that is redder than plants of 'Atomic Pink'.

In addition the new cultivar can be compared to the commercially available cultivar 'Purpleicious', U.S. Plant Pat. No. 17,639. However, in comparison, plants of the new cultivar 'Atomic Silvery Pink Ray' differ from plants of 'Purpleicious' in at least the following characteristics:

1. Plants of the new cultivar have a flower color that is redder than plants of 'Purpleicious';
2. Plants of the new cultivar are taller than plants of 'Purpleicious'; and
3. Plants of the new cultivar are less branched than plants of 'Purpleicious'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Atomic Silvery Pink Ray'. The plant was field grown for approximately 2 years in Haarlem, The Netherlands in an outdoor nursery location. The plant was transplanted into a container for photography purposes.

DETAILED BOTANICAL DESCRIPTION

Figure 1:
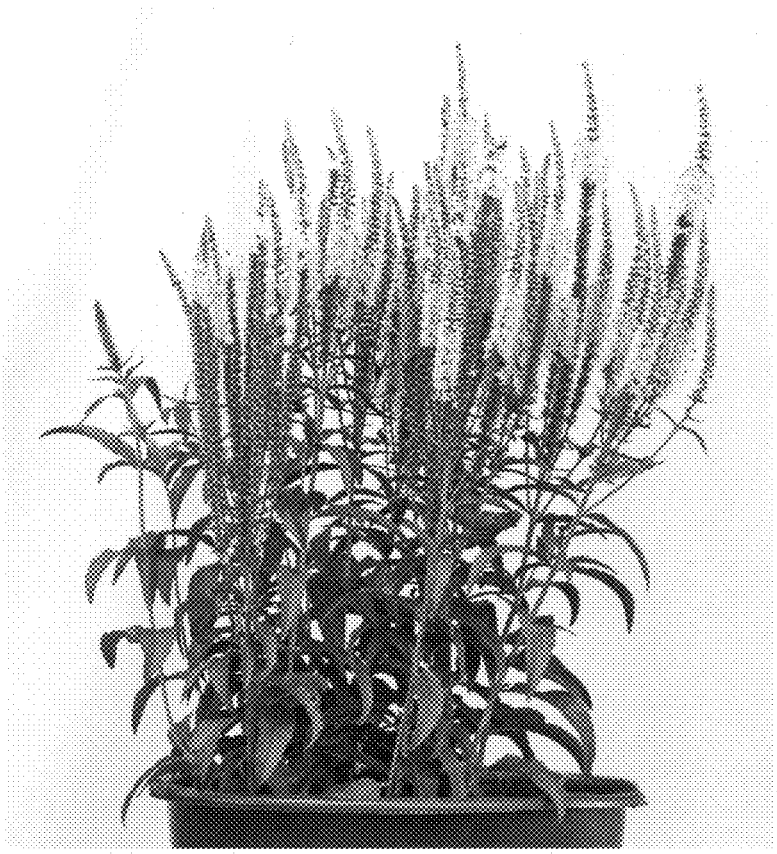
FIG. 1 illustrates a side view of the overall growth and flowering habit of 'Atomic Silvery Pink Ray'.
Figure 2:
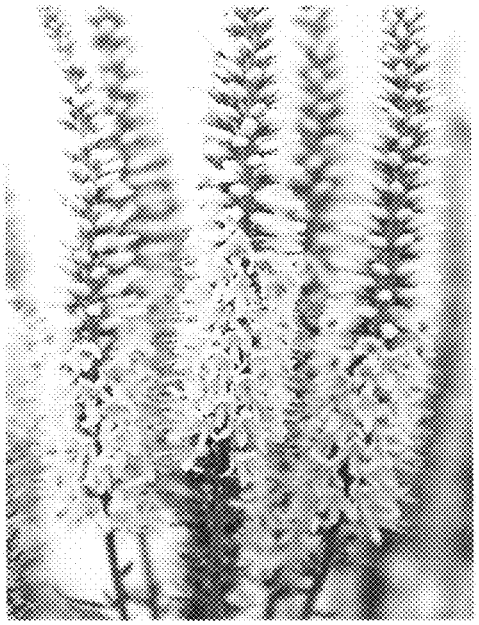
FIG. 2 illustrates a close-up view of an individual inflorescence of 'Atomic Silvery Pink Ray'.
Figure 3:
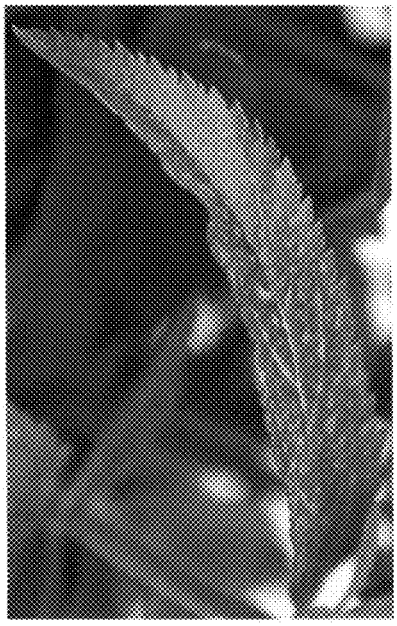
FIG. 3 illustrates a close-up view of the foliage of 'Atomic Silvery Pink Ray'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The data which define these characteristics were collected from asexual reproductions carried out in Haarlem, The Netherlands. The plant history was taken in August 2011 on 2-yearold field grown plants which were planted and grown outdoors in daytime temperatures between 14° C. and 28° C. and nighttime temperatures between 5° C. and 18° C. No pinching, growth retardants or photoperiodic treatments were used. Observations were made when the plants were in natural daylight conditions.

Botanical classification: *Veronica hybrida* cultivar 'Atomic Silvery Pink Ray'.

Parentage:

*Female parent.*—Unknown *Veronica hybrida.*

*Male parent.*—Unknown *Veronica hybrida.*

Propagation:

*Type cutting.*—Vegetative cutting.

*Time to produce a rooted cutting.*—Approximately 30 days with average soil temperature of 14° C.

*Root description.*—Fine, fibrous; grey in color.

*Rooting habit.*—Moderate density, poorly branching.

Plant description:

*Type.*—Herbaceous perennial. Overall shape: Narrow inverted triangle. High temperature tolerance: Tolerant to at least 35° C. Low temperature tolerance: Hardy to at least USDA Zone 4. Excellent garden performance.

*Commercial crop time.*—Approximately 4 months from rooted cutting to a finish flowering plant.

*Growth habit and general appearance.*—Upright, moderately vigorous.

*Size.*—Height from soil level to top of plant plane: Approximately 54.5 cm. Width: Approximately 36.8 cm. Rate of growth: In spring, approximately 12 cm per month.

*Branching habit.*—Freely basal branching. Pinching not required, but will improve basal branching. Quantity of branches per plant: Approximately 12.

*Branches.*—Shape: Rounded. Strength: Strong. Aspect: Erect. Length to base of inflorescence: Approximately 27.4 cm. Diameter: Approximately 4.0 mm. Length of central internode: Approximately 3.1 cm. Texture: Slightly glossy, densely pubescent with short greenish-white hairs. Length of pubescence: Approximately 0.5 mm. Color of young and mature stems: 138B with 144B.

Foliage description:

*General description.*—Quantity of leaves per stem: Approximately 14. Form: Simple. Arrangement: Opposite. Durability to stress: High.

*Leaves.*—Shape: Narrowly ovate to lanceolate. Margin: Serrate with approximately 4 teeth per cm. Apex: Acute. Base: Attenuate. Venation pattern: Pinnate. Length of mature leaf: Approximately 8.1 cm. Width of mature leaf: Approximately 2.4 cm. Texture of upper surface: Moderately glossy, sparsely pubescent with short greenish-white hairs of approximately 0.2 mm in length. Texture of lower surface: Moderately glossy, moderately pubescent with short greenish-white hairs of approximately 0.4 mm in length. Color of upper surface of young foliage: 137B and venation of 143C. Color of lower surface of young foliage: 138B with venation of 143B to 143C. Color of upper surface of mature foliage: Between N137D and 147A with venation of 143C. Color of lower surface of mature foliage: 147B and venation of 143B to 143C.

*Petiole.*—Shape: V-shaped. Length: Approximately 7.0 mm. Width: Approximately 2.0 mm. Height: Approximately 2.0 mm. Color: 144A.

Flowering description:

*Flowering habit.*—Freely flowering under outdoor growing conditions with substantially continuous blooming from July through mid-October in The Netherlands.

*Lastingness of individual flower on the plant.*—Approximately 7 days.

*Flowering response time.*—Approximately 60 days.

Inflorescence description:

*General description.*—Type: Terminal raceme, self-cleaning. Fragrance: Faint. Height: Approximately 25.1 cm for main inflorescences and approximately 20.2 cm for secondary inflorescences. Width: Approximately 2.3 cm. Quantity of opened flowers per inflorescence: Approximately 440 for main inflorescences and approximately 320 for secondary inflorescences. Rate of flower opening: Approximately 20% of the flowers open at any stage.

*Peduncle.*—Strength: Strong. Aspect: Main inflorescences erect and secondary inflorescences at approximately 20° angle from vertical. Length: Approximately 24.7 cm for main inflorescences and approximately 19.8 cm for secondary inflorescences. Diameter: Approximately 3.0 mm for main inflorescences and approximately 2.0 mm for secondary inflorescences. Texture: Smooth, glabrous. Color: 138B with 144B.

Flower description:

*General description.*—Type: Single. Shape: Campanulate. Aspect: Outward.

*Bud just before opening.*—Quantity per inflorescence: Approximately 1,400. Shape: Ovoid. Length: Approximately 6.5 mm. Diameter: Approximately 2.5 mm. Color: 65B. Rate of opening: Approximately 20% of buds open at once, all open within approximately 8 weeks.

*Corolla.*—Shape: Campanulate. Height: Approximately 9.0 mm. Diameter: Approximately 8.0 mm.

*Petals.*—Quantity: 4. Arrangement: Approximately lower 40% of each petal fused into a narrow tube. Appearance: Dull. Shape: Elliptic. Margin: Entire. Apex: Obtuse. Length: Approximately 7.0 mm. Width: Approximately 2.0 mm with upper petal approximately 3.5 mm. Texture of upper and lower surfaces: Smooth, glabrous. Color of upper surface when first open: 62C to 65B. Color of lower surface when first open: 65B. Color of upper surface when fully open: 62C to 65B, fading to 69B to 69C. Color of lower surface when fully open: 65B.

*Calyx.*—Shape: Rotate. Length: Approximately 3.0 mm. Diameter: Approximately 3.0 mm.

*Sepals.*—Quantity: 4. Appearance: Dull. Shape: Narrowly ovate. Margin: Entire. Apex: Acute. Base: Cuneate, lower 10% fused. Length: Upper sepals approximately 2.0 mm with lower sepals of approximately 3.0 mm. Width: Approximately 1.0 mm. Texture of upper and lower surfaces: Smooth. Color of upper and lower surfaces of immature sepals: 137C. Color of upper and lower surfaces of mature sepals: 137C.

*Pedicel.*—Strength: Strong. Aspect: Approximately 60° angle from vertical. Length: Approximately 1.0 mm. Diameter: Approximately 0.5 mm. Texture: Smooth, glabrous. Color: 144B.

*Reproductive organs.*—Androecium: Stamen quantity: 2 per flower, dorsifixed. Anther shape: Elliptic. Anther length: Approximately 2.0 mm. Filament length: Approximately 6.0 mm. Anther color: 71A to 71B. Filament color: 69A. Pollen amount: Sparse. Pollen color: 159B. Gynoecium: Pistil quantity: 1 per flower. Pistil length: Approximately 8.0 mm. Stigma shape: Clavate. Stigma color: 156C to 156D. Style length: Approximately 7.5 mm. Style color: 72B transitioning to 72D towards base. Ovary color: 144B.

Seed and fruit production: Neither seed nor fruit production has been observed.

Disease and pest resistance: Good mildew and rust resistance. No particular resistance or susceptibility to other diseases or insects noted to date.

What is claimed is:

1. A new and distinct cultivar of *Veronica* plant named 'Atomic Silvery Pink Ray', substantially as herein shown and described.

* * * * *